United States Patent [19]

Snow

[11] Patent Number: 5,146,925
[45] Date of Patent: Sep. 15, 1992

[54] CHOLANGIOCATHETER AND DELIVERY SYSTEM

[76] Inventor: Lamar Snow, 125 Louiselle St., Mobile, Ala. 36607

[21] Appl. No.: 616,941

[22] Filed: Nov. 21, 1990

[51] Int. Cl.$^5$ .......................................... A61M 25/00
[52] U.S. Cl. ................... 128/658; 604/104; 604/51; 604/280
[58] Field of Search ............... 604/51, 164, 264–266, 604/43, 96, 280, 190, 104, 167; 128/655–658

[56] References Cited

U.S. PATENT DOCUMENTS

| | | | |
|---|---|---|---|
| 2,927,584 | 3/1960 | Wallace | 604/96 |
| 3,659,611 | 5/1972 | Miller | 604/104 X |
| 3,721,229 | 3/1973 | Ranzer | 128/658 |
| 3,880,168 | 4/1975 | Berman | 128/207.15 |
| 3,918,456 | 11/1975 | Patel | 604/280 |
| 4,263,917 | 4/1981 | Moss | 128/656 |
| 4,299,226 | 11/1981 | Banka | 606/194 X |
| 4,306,566 | 12/1981 | Sinko | 128/658 |
| 4,747,823 | 5/1988 | Buchanan | 604/49 |
| 4,787,882 | 11/1988 | Clarén | 604/4 |
| 4,909,787 | 3/1990 | Danforth | 604/95 |
| 5,041,111 | 8/1991 | Bauer et al. | 604/167 |

Primary Examiner—C. Fred Rosenbaum
Assistant Examiner—Adam J. Cermak
Attorney, Agent, or Firm—Cushman, Darby & Cushman

[57] ABSTRACT

A self anchoring catheter and delivery system therefor for performing cholecystectomies through a laparoscope so that the catheter can be properly delivered to the cystic duct and so that the catheter will not undesirably fall out of the cystic duct during the cholangiogram. The anchoring portion can be an inflatable balloon which is inflated only when a material is injected through the catheter into the cystic duct. In the alternative, the anchoring portion can be a hub formed from a foam rubber or cellular plastic material which is compressible and has a non-smooth exterior surface whereby the anchoring portion will snugly engage and frictionally retain the catheter within the cystic duct until a positive force is applied to withdraw the same from the duct. The self anchoring catheter is delivered to the cystic duct through a delivery sleeve which is sized so as to be insertable through a standard laparoscope introducer sheath. The distal end of the sleeve can be straight or can be jointed to allow the distal end to be bent to allow directional control of the catheter into the cystic duct. The bendable delivery sleeve or sheath has other applications in the field of intra-abdominal surgery. Indeed, the delivery sleeve, alone, can be used as a disposable laparoscopic directional tip suction device, to house a laser fiber delivery system, or to house a cautery device.

26 Claims, 4 Drawing Sheets

CHOLANGIOCATHETER AND DELIVERY SYSTEM

BACKGROUND OF THE INVENTION

1. Field of the Invention

The present invention relates to gallbladder surgery and, more particularly, to a self anchoring cholangiocatheter and a flexible joint delivery system therefor. The flexible joint delivery system configuration can also be used for other devices employed during gallbladder surgery or other intra-abdominal surgical procedures.

2. Description of the Related Art

A cholangiogram is an X-ray image of the main liver ducts or Biliary Ducts following contrast media injection. The Biliary Ducts consist of the intra-hepatic biliary radicals, the left and right main hepatic ducts which are formed by the merged biliary radicals, and the single main hepatic duct defined by the merged right and left hepatic ducts. The gallbladder empties into the main hepatic duct to form therewith the common bile duct which in turn empties into the small intestine. A cholangiogram is performed to determine whether any stones are disposed in the main duct system.

A cholangiogram is obtained by making a small incision in the side of the cystic duct, which leads from the gallbladder to the main hepatic duct, and inserting a catheter thereinto through which a radiopaque liquid is injected while an X-ray is taken. The X-ray image shows any stones in the duct system which must be removed. The stones, if any, are removed by a further surgical procedure. It is important to determine whether stones are present in the main duct system because such stones may cause blockage which prevents the liver from excreting bile. The bile would then back up into the blood stream causing jaundice and may eventually lead to death.

Conventionally, the foregoing catheter insertion was performed through a large open incision which allowed the doctor to manually insert the catheter into the cystic duct. The catheter would then be tied within the duct with a suture to prevent it from falling out during the cholangiogram. That invasive technique required a lengthy hospital stay and resulted in significant scarring.

Recently, cholecystectomies have been performed though a laparoscope rather than through such a large open incision. However, this new procedure has the disadvantage that there is no good method of anchoring the catheter within the cystic duct and hence the catheter may fall out during the procedure.

SUMMARY OF THE INVENTION

The present invention provides a self anchoring catheter and delivery system therefor for performing, for example, cholecystectomies through a laparoscope so that the catheter can be properly delivered to the cystic duct and so that the catheter will not undesirably fall out of the cystic duct during the cholangiogram.

The self anchoring catheter of the invention is a semi-rigid tubular element having an anchoring portion defined thereon adjacent a distal end thereof. The anchoring portion is formed from a foam or sponge rubber or cellular foam plastic or polymeric material which is compressible and has a non-smooth exterior surface whereby the anchoring portion will snugly engage and frictionally retain the catheter within the cystic duct until a positive force is applied to withdraw the same from the duct.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings of which form a part of this specification, wherein like reference numerals designate corresponding parts in the various figures.

BRIEF DESCRIPTION OF THE DRAWINGS

FIG. 7 is a schematic elevational view of an alternate embodiment of a bendable sheath provided in accordance with the present invention;

DETAILED DESCRIPTION OF THE PRESENTLY PREFERRED EXEMPLARY EMBODIMENTS

Figure 1:
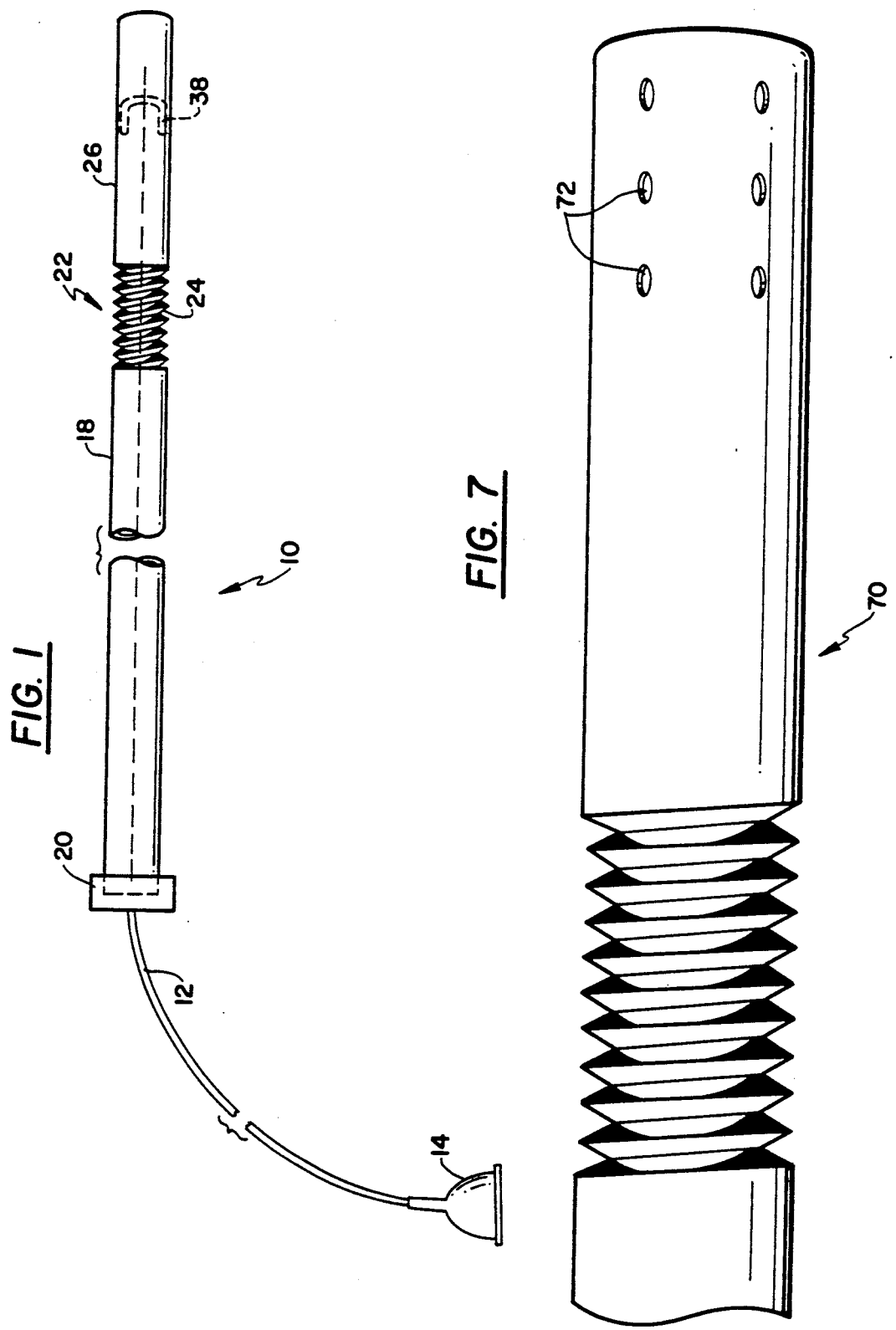
FIG. 1 is a schematic elevational view of a catheter assembly provided in accordance with the present invention.

A complete catheter system 10 provided in accordance with the present invention is shown by way of example in FIG. 1. The contrast media delivery catheter is a semi-rigid plastic catheter 12 having a proximal end provided, for example, with a standard Luer-Lok type syringe connector 14 and a slightly tapered distal end 16 (FIGS. 3-6 and 10) which is adapted to be inserted into the cystic duct. As is apparent, providing a tapered distal end facilitates insertion of the catheter into the cystic duct and, in particular, into small size ducts. The particular material used to form the catheter of the invention can be selected from known biocompatible plastic materials which have sufficient structural integrity to allow the catheter to be inserted into the cystic duct under a certain amount of pressure without bending yet exhibit sufficient flexibility to navigate the angle into the common duct without damaging that duct. During a major portion of the procedure, the catheter of the invention will remain in the cystic duct. In accordance with the most preferred embodiment of the invention, the catheter is approximately 16 inches in length and for most purposes could be provided in size 3, 4 or 5 French.

As described in greater detail below, the self anchoring catheter of the invention is delivered to the cystic duct through a relatively stiff sleeve or sheath 18 which is sized so as to be insertable through a standard 5 millimeter laparoscope introducer sheath (not shown). In accordance with the preferred embodiment of the invention the stiff sleeve 18 is plastic and is disposable. It is to be understood, however, that any suitable material can be used for the sleeve or sheath 18 of the invention, including a material which can be re-sterilized so that the sleeve can be re-used.

As illustrated in FIG. 1, the proximal end of the delivery sleeve 18 has a fenestrated rubber plug 20 through which the catheter 12 of the invention may slide distally and proximally but which prevents escape of intra-abdominal gas. The distal end of the sleeve 18 can be straight or can be jointed as shown at 22 in FIG. 1 to allow the distal end to be bent relative to the longitudinal axis of the sleeve 18 to thereby allow directional control of the catheter 12 into the cystic duct. While a variety of structures can be used to provide a controllably jointed tip in accordance with the present invention, in the illustrated embodiment the delivery sleeve has an accordion joint 24 similar to the accordion joint provided in flexible drinking straws. The accordion joint 24 is formed in the wall of the tube defining the delivery sleeve 18, approximately 1 inch from the distal most end thereof. The tip 26 can be oriented to virtually any angle straightened simply by pressing the distal tip 26 of the sleeve or sheath 18 against any object or structure within the patient's abdominal cavity. When the sheath is used to deliver a catheter during a cholecystectomy, this allows formation of a perfect angle for insertion of the self anchoring catheter into the cystic duct. Indeed, mobility through the laparoscope is limited and on occasions the angle between the cystic duct and the catheter makes insertion difficult. By providing a delivery sheath 18 having a distal most end 26 which can be adjustably inclined with respect to the longitudinal axis of the sheath, delivery of the catheter 12 to the cystic duct and insertion thereinto can be facilitated.

As described in greater detail below, the bendable delivery sleeve or sheath of the invention has other applications in the field of gall bladder surgery and other intra-abdominal surgical procedures. Indeed, the delivery sleeve, alone, can be used as a disposable laparoscopic directional tip suction device. In the alternative, the sleeve can house a laser fiber delivery system or it can house a cautery device.

Figure 2:
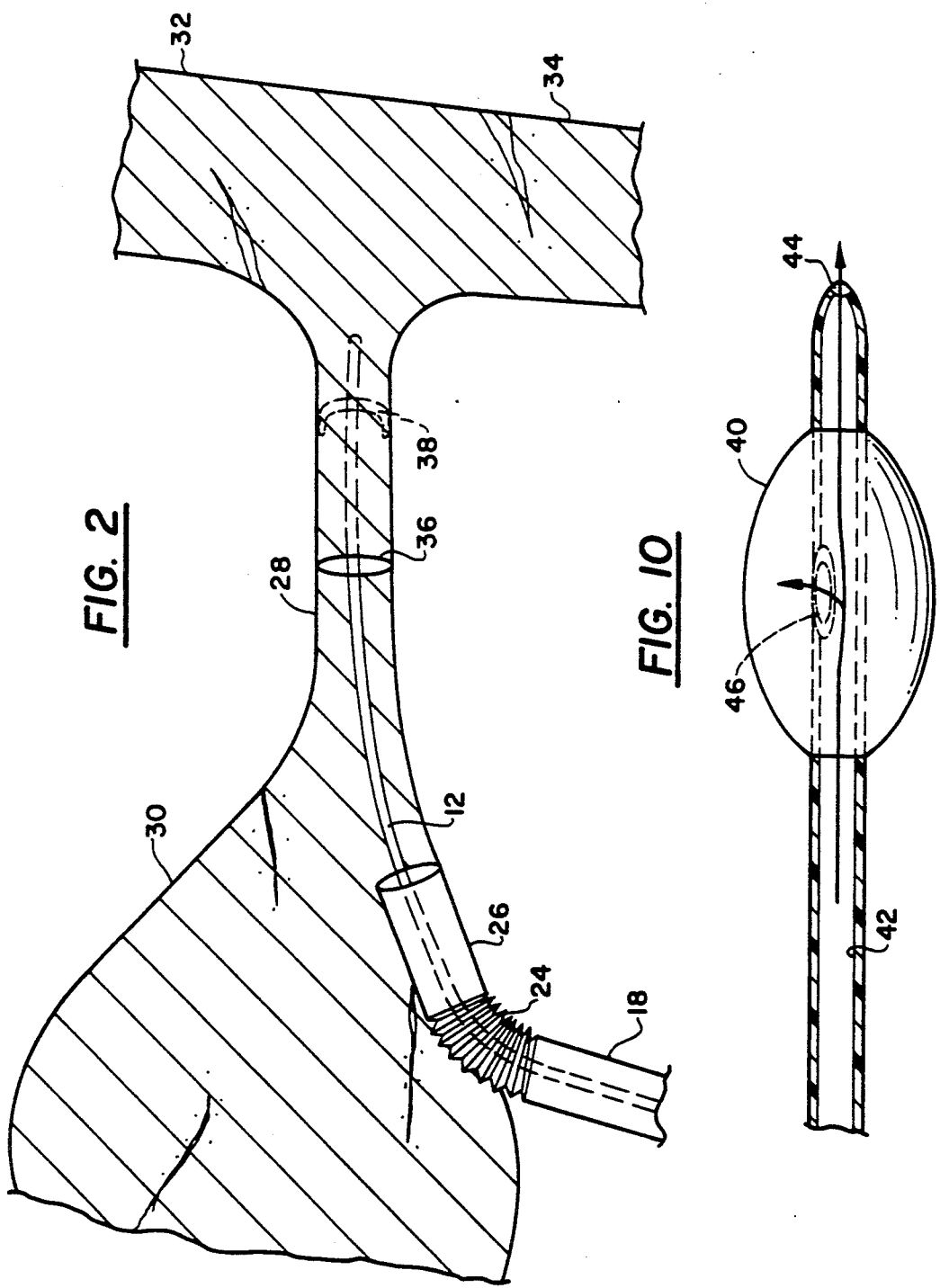
FIG. 2 is a schematic elevational view of the insertion of a self anchoring catheter into the cystic duct.

With reference in particular to FIG. 2, the catheter 12 of the invention is delivered to the cystic duct 28 as follows. A laparoscopic introducer sheath (not shown) is inserted through the abdominal wall. An incision 36 is then made in the wall of the cystic duct 28 which leads from the gall bladder 30 to the main hepatic duct 32 to form therewith the common bile duct 34. The catheter assembly 10 of the invention, illustrated by way of example in FIG. 1, is then inserted through the laparoscopic introducer sheath until the distal tip of the delivery sheath 18 is adjacent the incision 36 in the cystic duct 28. The distal end of the sheath is urged against an intra-abdominal structure to bend the same relative to the longitudinal axis of the sheath. The accordion formation 24 in the wall of the sheath 18 enables the distal end 26 to be bent and maintains the distal end 26 in that bent configuration until a straightening force is applied thereto.

With the delivery sheath 18 bent to the proper angle, the catheter 12 of the invention is advanced through the distal end of the sheath and through the incision 36 into the cystic duct 28. In accordance with the embodiments of FIGS. 3–6, as the distal end of the catheter 12 is urged into the cystic duct 28, engagement of the exterior surface of the anchoring portion 38 of the catheter 12 with the wall of the cystic duct 28 will hold the catheter 12 in position within that duct once the insertion is force is removed. The catheter 12 will be held in position by the anchoring portion thereof until a force is applied to that catheter to further advance the catheter 12 into the common duct 34 or to withdraw the catheter 12 from the cystic duct 28 entirely.

In accordance with the embodiment of FIG. 10, described in greater detail below, when the distal end of catheter 12 is urged into the cystic duct 28, the catheter 12 is not initially anchored within the duct. However, when contrast media or a radiopaque dye is injected through the catheter as described more fully below, the inflatable balloon 40 mounted thereto is inflated so as to anchor catheter 12 within the cystic duct 28. Once injection of the radiopaque dye has been completed, the balloon 40 will deflate, allowing the catheter to be further advanced or retracted from the cystic duct 28.

Once the catheter 12 is in place within the cystic duct 28, a radiopaque dye is injected through the catheter and an X-ray image of the duct system is obtained. As noted above, in accordance with the embodiment of FIG. 10, injection of the radiopaque dye will inflate balloon 40 thereby anchoring catheter 12 within the cystic duct until injection of the radiopaque dye has been completed. Once the procedure has been completed, the catheter 12 is withdrawn from the cystic duct 28 into the delivery sleeve 18, the delivery sleeve 18 is straightened by urging the distal end against an intra-abdominal structure to straighten the accordion section 24 and the entire catheter assembly 10 is removed through the laparoscopic sheath. In the alternative, the delivery sheath can be retained with the abdomen and the catheter 12 removed from therewithin so that subsequent instruments as necessary can be advanced therethrough.

The self anchoring portion provided adjacent the distal end of the catheter of the invention can be provided in any of a number of anchoring configurations. Exemplary configurations are shown in FIGS. 3–6 and 10. While the location of the anchoring portion may be varied without departing from the concept of the invention, it is envisioned that in accordance with the most preferred embodiment, the anchoring portion is defined approximately 8 millimeters from the distal most tip of the catheter. In accordance with the embodiment of FIG. 10, the anchoring balloon can be formed from any suitable thin polymeric or rubber material. In particular, the balloon can be formed from an expansible and retractable or stretchy material or from a inflatable and collapsible, relatively non-resilient material. In accordance with the embodiments of FIGS. 3–6, the anchoring portion of the catheter of the invention can be formed from any known foam or sponge rubber or cellular foam plastic or polymeric material that exhibits suitable structural and functional characteristics as outlined below. As will be apparent, the desired characteristics of the anchoring portion vary somewhat depending upon the configuration of that portion of that catheter. The material selected for the anchoring portion of FIGS. 3–6 should be of sufficient resiliency and flexibility to allow approximately 50% compression of the material and still be insertable into the duct without a force sufficient to bend the catheter. Further, the surface of the anchoring portion should be sufficiently rough to allow frictional engagement with the inner wall of the cystic duct to retain the catheter in position.

Where the anchoring portion is molded on the catheter, the smooth surface thereof, which would have reduced anchoring capacity, should be cut or otherwise treated to increase its roughness and hence enhance the frictional retention made possible thereby. Other methods of forming the anchoring portion or mounting the same on the main body of the catheter will inherently provide an exterior surface exhibiting sufficient frictional characteristics.

As shown in FIG. 10, the anchoring portion 38 of the catheter 12 of the invention can be in the form of an inflatable balloon 40 mounted to the exterior surface of the catheter tube. A single lumen 42 is defined centrally through the tube of catheter 12 and terminates distally in an aperture 44 so that radiopaque dye can be injected through the catheter into the biliary ducts. A port 46 is defined through the side wall of catheter 12 and communicates between the lumen 44 and the interior of inflatable balloon 40. Because the interior of balloon 40 communicates directly with lumen 44 rather than with its own inflation passage, balloon 40 will be inflated when a radiopaque dye or other material is injected through catheter 12. Thus, the balloon is inflated simultaneously with delivery of material through the catheter into, for example, the cystic duct. Likewise, when injection through catheter 12 has been completed, the balloon 40 will deflate. Thus, in accordance with the embodiment of FIG. 10, the catheter 12 is anchored in position within the cystic duct solely during injection of the contrast media and the catheter can be readily removed or further inserted at any other time.

Figure 3:
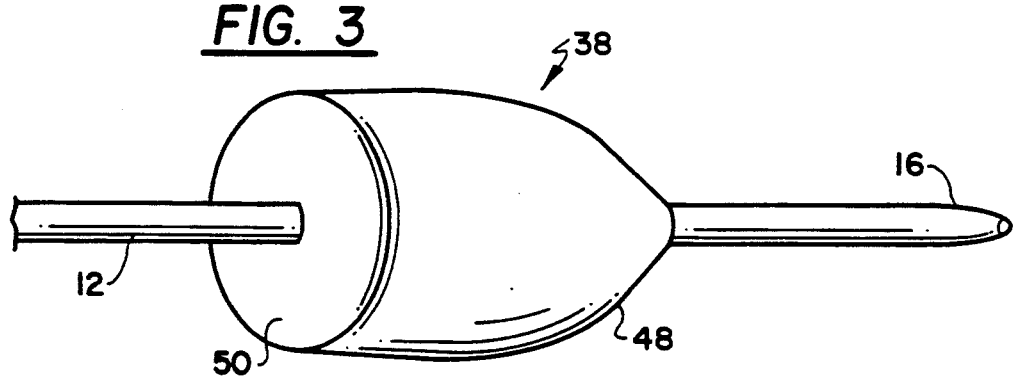
FIG. 3 is a schematic perspective view of a first embodiment of the anchoring portion of the catheter formed in accordance with the present invention.

As shown in FIG. 3, the anchoring portion 38 of the catheter 12 of the invention can be in the form of a "arrow" having an inclined forward edge portion 48 which facilitates insertion thereof into the cystic duct 28 and a planar rear edge 50 which tends to resist removal of the catheter 12 unless a sufficient withdrawing force is applied thereto. The external diameter of the arrow-shaped hub should provide for engagement of the walls of the cystic duct with sufficient force to retain the catheter in position. In accordance with the preferred embodiment of the invention it is envisioned that for a 3 French catheter the maximum diameter of the arrow-shaped hub should be approximately 4 millimeters. The hub diameter should be approximately 5 millimeters for a 4 French catheter and approximately 6 millimeters for a 5 French catheter. Of course the dimensions can be varied depending upon the size of the duct itself and required force to maintain the catheter in position.

Figure 4:
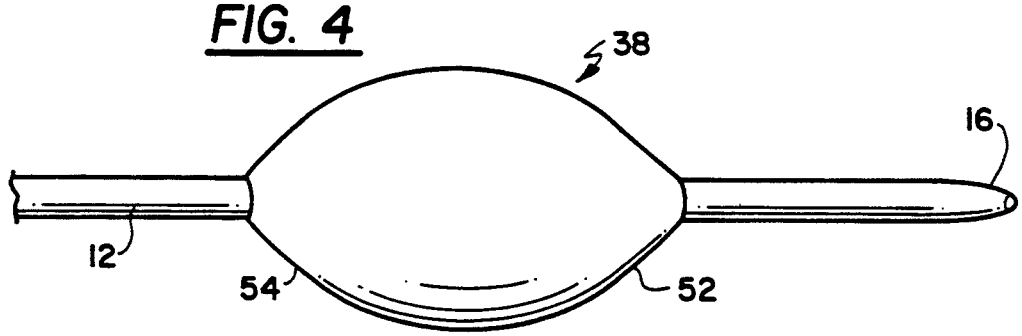
FIG. 4 is a schematic perspective view of a second embodiment of the anchoring portion of the catheter.

As an alternative, the anchoring portion provided in accordance with the present invention can be a bulbous hub as illustrated in FIG. 4. The inclined forward and rearward portions 52, 54 of the bulbous hub facilitate both insertion and removal of the catheter from the cystic duct 28 and facilitate dilation of the duct and compression of the hub to ensure secure engagement between the bulbous portion and the wall of the duct.

The anchoring configurations illustrated in FIGS. 3 and 4 are sufficient to anchor the catheter in most if not all cases. However, to enhance the anchoring of the catheter of the invention, in addition to compression and friction, the hub can be in the form of a disc or flange so that insertion of the catheter will fold back a portion of the anchoring hub to produce a barb which allows forward movement but resists backward movement of the catheter 12 within the duct 28. The embodiments illustrated in FIGS. 5 and 6 provide such a flange/barb retention structure.

Figure 5:
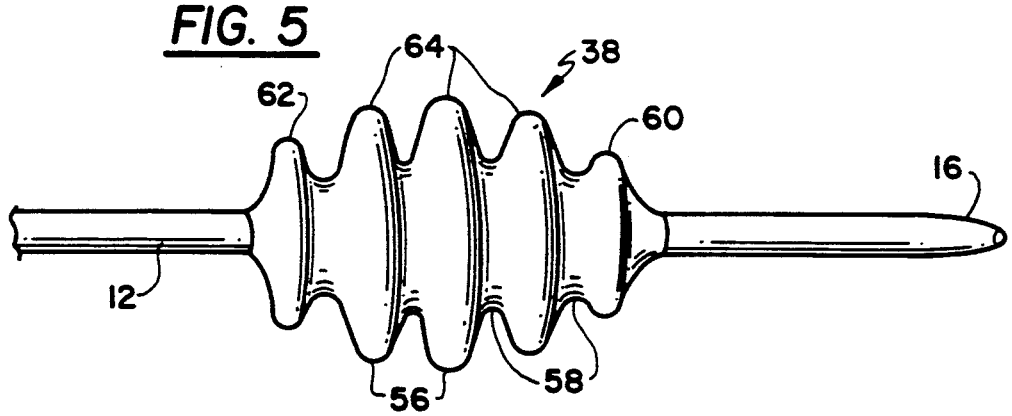
FIG. 5 is a schematic perspective view of a third embodiment of the anchoring portion of the catheter.

As illustrated in FIG. 5, the anchoring hub portion 38 of the invention can be a series of flanges 56 of various diameters. The flanges may be provided as distinct elements on the catheter or can be structurally interconnected with collar portions 58 as shown in FIG. 5. Where a plurality of flanges 56 are provided, the forward most flange 60 preferably has a smaller diameter than the remaining flanges. The rearward most or proximal most flange 62 can be either the largest flange of the assembly or can be of approximately the same size as the forward most flange 60, as illustrated in FIG. 5. The diameter of the intermediate flange elements 64 can be varied as desired but the largest flange preferably has a diameter slightly greater than the maximum external diameter of the anchoring hub portions of each of FIGS. 3 and 4 to encourage the deflection of the outer most edge of that flange upon insertion of the catheter.

Figure 6:
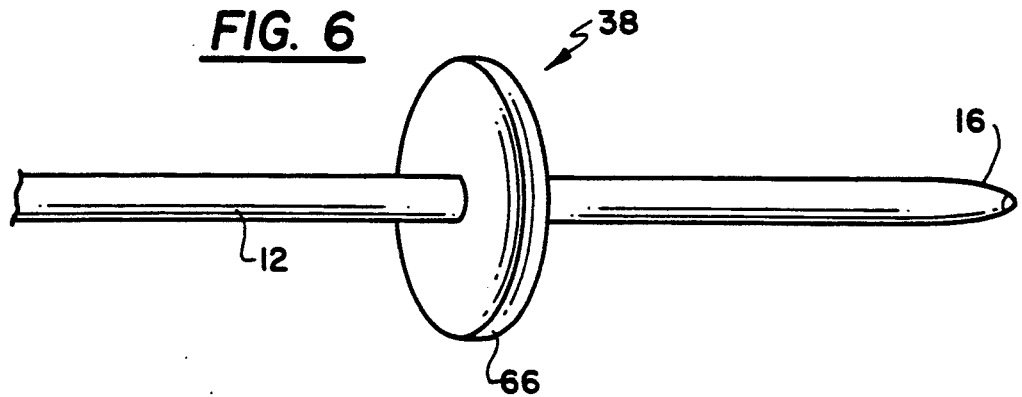
FIG. 6 is a schematic perspective view of a fourth embodiment of the anchoring portion of the catheter.

As illustrated in FIG. 6, a single flange 66 can be provided on the catheter to provide the barb-type anchoring of the catheter. As is apparent, upon insertion of the catheter of FIG. 6, the disc or flange 66 will fold back on itself producing a barb allowing forward movement but resisting backward movement of the catheter 12. When it is desired to remove the catheter, an extra tug on the proximal end of the catheter will reverse the barb direction allowing removal of the catheter with the same force as insertion.

As is apparent from the foregoing, the anchoring hub portion 38 provided adjacent the distal most end of the contrast media delivery catheter will retain the catheter in position within the cystic duct until a positive force is applied to the catheter to remove it therefrom. As is further apparent, a variety of configurations for the anchoring hub portion can be provided, each of which will advantageously anchor the catheter of the invention within the cystic duct. Accordingly configurations other than those specifically illustrated could be provided without departing from the concept of this invention.

As mentioned above, the relatively rigid delivery sleeve or sheath 18 provided in accordance with the present invention can be used for devices and procedures associated with intraabdominal surgery, other than the delivery of a catheter during cholecystectomies.

Thus, as illustrated in FIG. 7, the sheath of the invention can be used as a disposable laparoscopic flexible tip suction device 70. The suction device 70 is substantially similar to the delivery sheath 18 for the catheter of the invention and in fact the same structure may be used for both functions. However, when the delivery device is to be selectively used as a suction device, additional apertures 72 should be defined adjacent the distal tip to prevent blockage of the sheath 70 when suction is applied therethrough. Thus in the illustrated embodiment nine holes 72 are provided adjacent the distal most end of the sheath 70. The particular number and disposition of apertures, of course, can be varied from the nine aperture configuration shown without departing from the invention.

While the length of the sheath provided in accordance with the invention can be varied without altering the advantageous characteristics thereof, it is envisioned that when the sheath is utilized as a delivery device 18 it should have a length of approximately 10 inches whereas when employed as a suction device 70 a length of about 14 inches would be most preferred. Suction can be applied to the sheath 70 of the invention through the proximal most end if the fenestrated washer is removed therefrom or could be applied through a side port of the type illustrated in FIG. 8.

The bendable tip sheath of the invention can further be utilized as a laser fiber delivery system 74. This embodiment of the invention is shown in particular in FIG. 8. As can be seen, the sheath of this embodiment is substantially similar to that illustrated in FIGS. 1 and 7, having a fenestrated rubber washer 76 provided at the proximal end thereof and an accordion section 78 adjacent the distal end thereof. As disclosed above, the accordion section 78 allows the distal most tip to be oriented at an angle with respect to the longitudinal axis of the sheath and retained in that oriented configuration until a positive force is applied thereto. Further, as mention above with respect to FIG. 7, a side port 80 is defined through the wall of the sheath. A stop cock 82 is provided in the side port 80 for selectively providing suction or irrigation through the interior of the sheath. As with the embodiment of FIG. 7, a plurality of side holes or apertures 84 are defined at the distal most tip of the device to minimize the likelihood that the tip will become clogged in use.

Figure 8:
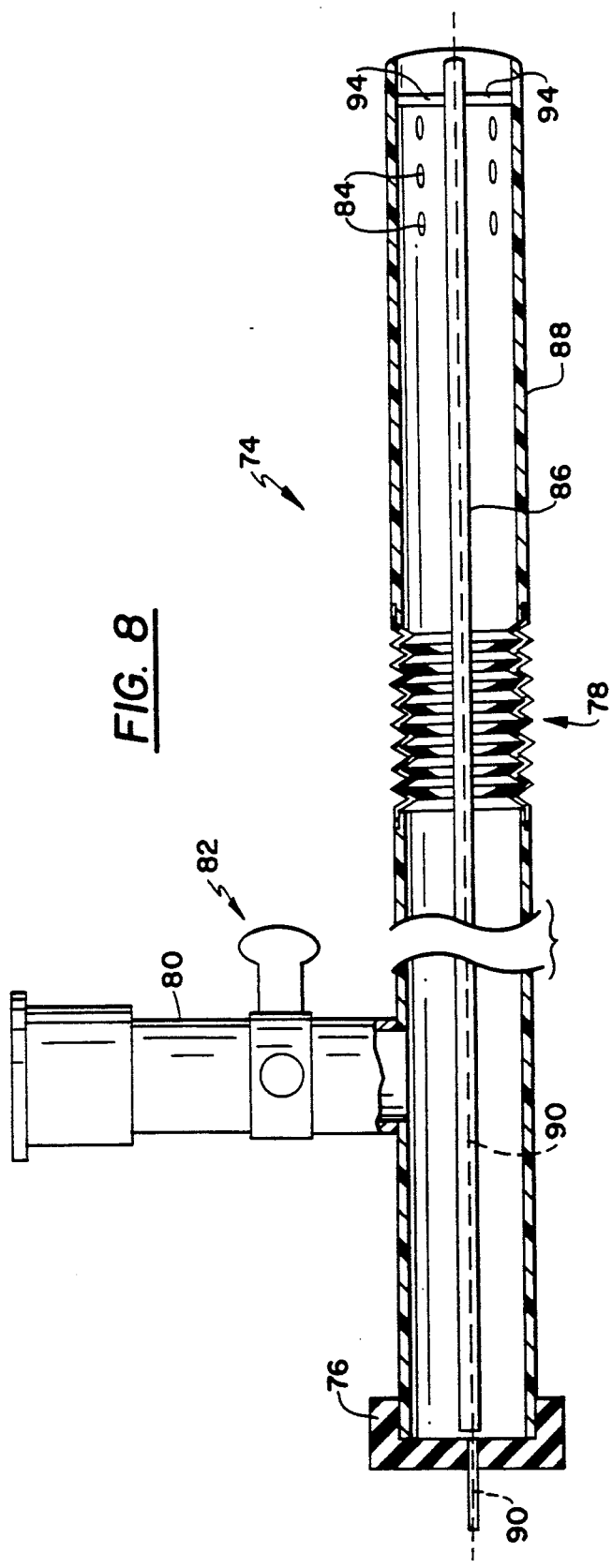
FIG. 8 is a schematic elevational view of a further form of the sheath.

In accordance with the embodiment of FIG. 8, an inner tube 86 is provided along the length of the sheath 88 to accommodate up to a 1,000 micron laser fiber 90. The laser fiber accommodating inner tube 86 is preferably formed from a semi-rigid plastic which can be deflected to accommodate a deflection in the accordion portion 92 of the sheath 88 and thus the angular disposition of the distal tip of the sheath. The inner tube 86 is supported at the distal most end of the sheath by tip supports 94 so that in use the laser fiber 90 will be centered within the sheath 88 if so desired. The suction-irrigator with laser fiber illustrated in FIG. 8 can be provided in any of a number of sizes but in accordance with the preferred embodiment both 5 millimeter and 7 millimeter diameter versions are provided each having a length of about 14 inches.

Figure 9:
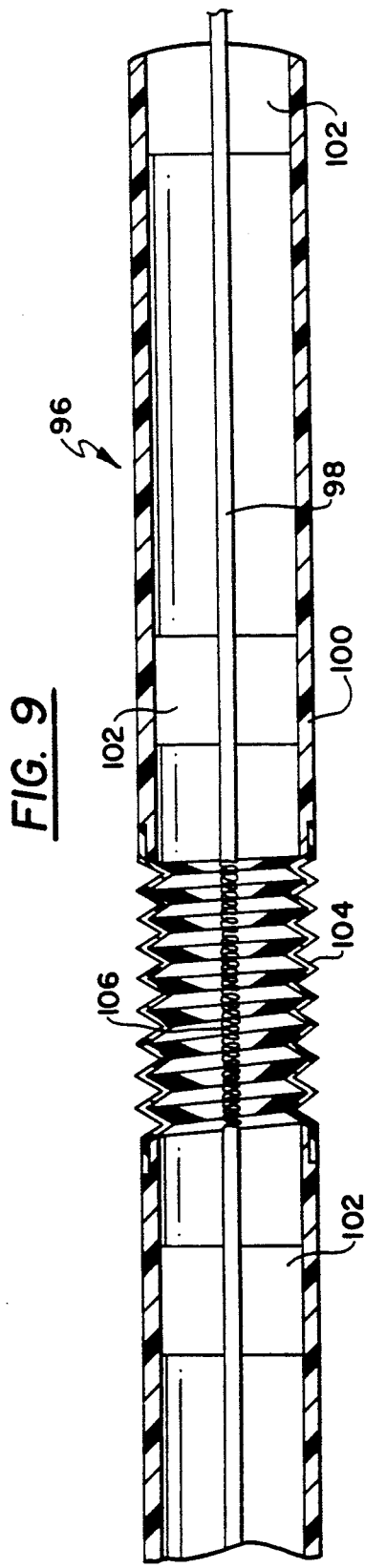
FIG. 9 is a schematic elevational view of a cautery device provided in accordance with the present invention.

In accordance with yet a further embodiment of the invention, a cautery device 96 can be provided, as shown in FIG. 9. In that embodiment, an electrode wire 98 is disposed centrally within the sheath 100 and is supported with respect thereto and maintained in a central disposition by a plurality of wire supports 102 defined along the length of the sheath 100. The electrode wire 98 can have any standard tip design provided at the distal most end thereof (not shown). In accordance with this embodiment, the accordion joint 104 is of sufficient stiffness to allow bending while still enabling light dissection. Bending of the sheath is followed by the electrode wire 98. Such bending of the electrode wire 98 can be facilitated by providing a flexible spring insert 106 along the portion of the length of the electrode wire corresponding to the accordion portion 104 of the sheath 100. In the illustrated embodiment, the accordion portion 104 is defined approximately 2 centimeters from the distal most end of the sheath.

As further shown in FIG. 9, the accordion joint portion 104 of the flexible sheath 100 can be formed as a separate segment and coupled in any suitable fashion to the remainder of the sheath. Thus the accordion joint can be formed from a material exhibiting characteristics different from that of the sheath tube itself. As is apparent, the accordion joint can be separately formed and attached to the sheath in any of the embodiments of the invention discussed above.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A self anchoring catheter comprising:
   a tubular main body portion having a proximal end, a distal end, and a longitudinal axis; and
   an anchoring hub portion defined on an exterior surface of said tubular main body portion adjacent said distal end, said anchoring hub portion being formed from a resiliently compressible material having a non-smooth exterior surface, said anchoring hub portion being formed from one of a foam rubber material and a cellular plastic material.

2. A catheter as in claim 1, wherein said anchoring hub portion has an arrow-shape having a substantially planer rearward end and an inclined forward end.

3. A catheter as in claim 1, wherein said anchoring hub portion has a bulbous shape having an inclined forward end, an inclined rearward end, a maximum diameter of said anchoring hub portion being defined substantially centrally between said forward and rearward ends.

4. A catheter as in claim 1, wherein said anchoring hub portion comprises at least one flange element extending radially outwardly from an exterior surface of said main body portion.

5. A catheter as in claim 4, wherein a plurality of flange elements are provided along a portion of the length of said tubular main body portion adjacent the distal end thereof.

6. A catheter as in claim 5, wherein at least one of said flange elements has a maximum diameter which is different than another of said flange elements.

7. A catheter as in claim 6, wherein a forward most flange element has a diameter less than another of said flange elements.

8. A catheter as in claim 4, wherein a single flange element is defined on the exterior surface of the catheter.

9. A catheter as in claim 1, in combination with a tubular sheath element having a proximal end, a distal end, and a longitudinal axis.

10. A combination as in claim 9, further comprising a resilient seal element mounted to said proximal end of said sheath element.

11. A combination as in claim 9, wherein said tubular sheath element has a circular cross-section.

12. The combination of a self anchoring catheter comprising:
   a tubular main body portion having a proximal end, a distal end, and a longitudinal axis, and an anchoring hub portion defined on an exterior surface of said tubular main body portion adjacent said distal end; and
   a tubular sheath element having a proximal end, a distal end, and a longitudinal axis, said tubular sheath element including an accordion portion defined along a portion of the length thereof so as to allow the distal end of said sheath element to be angularly offset with respect to said longitudinal axis, said accordion portion being defined so that the angular orientation of the distal end is retained until a force is applied thereto to alter said angular orientation.

13. A catheter as in claim 12, wherein said anchoring hub portion comprises an inflatable balloon mounted to said tubular main body portion, said tubular main body portion having an opening defined through the distal end thereof and a single lumen defined therethrough which terminates distally in said distal opening; and an inflation port defined through a wall of said tubular main body portion defining a flow path between said single lumen and the interior of said inflatable balloon.

14. A combination as in claim 12, further comprising a resilient seal element mounted to said proximal end of said sheath element.

15. A combination as in claim 12, wherein said tubular sheath element has a circular cross-section.

16. A sheath delivery device comprising:
   a substantially tubular element having a proximal end, a distal end, and a longitudinal axis;
   a resilient seal element mounted to said proximal end of said tubular element; and
   an accordion portion defined along a portion of the length of said tubular element whereby a portion of said sheath distal of said accordion portion can be offset with respect to said longitudinal axis, said angular offset being retained by said accordion portion until a positive force is applied to said distal portion.

17. A device as in claim 16, wherein said accordion portion is formed separately from the remainder of said tubular element and is fixedly coupled thereto.

18. A device as in claim 16, further comprising a side port extending radially from said tubular element and a valve means defined in said side port for controlling flow therethrough.

19. A device as in claim 16, further comprising an inner tubular member mounted within said tubular element and extending along the length thereof for slidably receiving a laser fiber.

20. A device as in claim 16, further comprising a plurality of apertures defined through the wall of said tubular element adjacent said distal end.

21. A device as in claim 16, further comprising an electrode wire mounted within said tubular element and extending along the length thereof.

22. A device as in claim 21, wherein said electrode wire includes a flexible spring portion, said flexible spring portion coinciding with said accordion portion of said tubular element so that said electrode wire can be bent as said distal portion of said tubular element is offset with respect to said longitudinal axis of said tubular element.

23. A method of obtaining a cholangiogram comprising:
   making an incision in the cystic duct of a patient;
   inserting a catheter comprising a tubular main body portion having a proximal end, a distal end, and a longitudinal axis; and an anchoring hub portion defined on an exterior surface of said tubular main body portion adjacent said distal end into said cystic duct, said anchoring hub being sized and shaped so as to engage the walls of the cystic duct thereby to retain the catheter in the duct and to seal the duct, said anchoring hub portion being formed from a resiliently compressible material having a non-smooth exterior surface, said anchoring hub portion being formed from one of a foam rubber material and a cellular plastic material;
   injecting a contrast media through said catheter into the biliary ducts of the patient;
   obtaining an X-ray image of said biliary ducts; and
   removing said catheter from the cystic duct.

24. A method as in claim 23, wherein said step of inserting a catheter comprises inserting a catheter assembly including said catheter disposed within a tubular sheath element having a proximal end, a distal end, and a longitudinal axis through the abdominal wall to a location proximate said cystic duct and advancing said catheter from said distal end of said tubular sheath element into said cystic duct.

25. A method as in claim 24, wherein said tubular sheath element further includes an accordion portion defined along a portion of the length thereof so as to allow the distal end of said tubular sheath element to be angularly offset with respect to said longitudinal axis thereof, said accordion portion being defined so that the angular orientation of the distal end is retained until a force is applied thereto to alter said angular orientation, and further comprising the step of angularly offsetting said distal end of said tubular sheath element with respect to said longitudinal axis thereof before said step of advancing said catheter from said distal end.

26. A method of obtaining a cholangiogram comprising:
   making an incision in the cystic duct of a patient;
   inserting a catheter comprising a main tubular body portion having a proximal end, and a distal end, and a longitudinal axis; and an anchoring hub portion defined on an exterior surface of said tubular main body portion adjacent said distal end into said cystic duct, said step of inserting comprising inserting a catheter assembly including said catheter disposed within a tubular sheath element having a proximal end, a distal end, a longitudinal axis and an accordion portion defined along a portion of the length thereof so as to allow the distal end of said tubular sheath element to be angularly offset with respect to said longitudinal axis thereof, said accordion portion being defined so that the angular orientation of the distal end is retained until a force is applied thereto to alter said angular orientation, through the abdominal wall to a location proximate said cystic duct;
   angularly offsetting said distal end of said tubular sheath element with respect to said longitudinal axis thereof;
   advancing said catheter from said distal end of said tubular sheath element into said cystic duct;
   injecting a contrast media through said catheter into the biliary ducts of the patient;
   obtaining an X-ray image of said biliary ducts; and
   removing said catheter from the cystic duct.

* * * * *